United States Patent [19]
Stevens et al.

[11] Patent Number: 5,897,874
[45] Date of Patent: Apr. 27, 1999

[54] EXPULSION OF MATERIAL FROM A DELIVERY DEVICE

[75] Inventors: Howard Norman Ernest Stevens, Drymen; Abdul Rashid; Massoud Bakhshaee, both of Glasgow; Julie Stephanie Binns, Chippenham; Christopher Jon Miller, Morpeth, all of United Kingdom

[73] Assignee: R. P. Scherer Corporation, Troy, Mich.

[21] Appl. No.: 08/663,076

[22] PCT Filed: Dec. 22, 1994

[86] PCT No.: PCT/GB94/02793

§ 371 Date: Sep. 20, 1996

§ 102(e) Date: Sep. 20, 1996

[87] PCT Pub. No.: WO95/17172

PCT Pub. Date: Jun. 29, 1995

[30] Foreign Application Priority Data

Dec. 23, 1993 [GB] United Kingdom ............... 9326267

[51] Int. Cl.⁶ .................. A61K 9/48; A61K 9/62

[52] U.S. Cl. .................. 424/451; 424/452; 424/453; 424/454; 424/458; 424/461; 514/772.3; 514/777; 514/778; 514/781; 514/951

[58] Field of Search .................. 424/452, 453, 424/454, 451, 458, 461

[56] References Cited

U.S. PATENT DOCUMENTS 5,342,624  8/1994  Mc Neill et al. ............ 424/451

Primary Examiner—Thurman K. Page
Assistant Examiner—James M. Spear
Attorney, Agent, or Firm—Gifford, Krass, Groh, Sprinkle, Anderson & Citkowski, P.C.

[57] ABSTRACT

A delivery device for delivering an active substance to a patient at a predetermined time after administration comprises a male hydrogel plug engaged in the neck of a female body. An expandable excipient such as a hydrogel powder or a pharmaceutical disintegrant in powder, slug or tablet form is provided beneath the active substance. In contact with an aqueous medium, the excipient absorbs water and swells such as to rapidly expel the active substance and effectively deliver it from the device.

17 Claims, 3 Drawing Sheets

EXPULSION OF MATERIAL FROM A DELIVERY DEVICE

This application is a 371 of PCT/GB94/02793 filed Dec. 22, 1994.

TECHNICAL FIELD

The present invention relates to the expulsion of a substance to be delivered from a hollow body of a delivery device. Particularly though not exclusively, the invention relates to the rapid and complete expulsion of an active material, such as a pharmaceutical drug formulation, from a capsule after the capsule has been administered to a patient.

BACKGROUND

International patent specification WO 90/09168 discloses a controlled release device for delivering a substance to a patient at a chosen time following administration. The device comprises a water-swellable male plug engaged within the female body. A pharmaceutically active material is contained within the device. When the device is exposed to water, the male hydrogel plug swells and eventually disengages itself from the female body, thereby allowing the pharmaceutically active material contained within the device to be released. It has been found that the time taken to disengage the hydrogel plug (e.g. 0.5 to 12 hours) is predictable and reproducible, so that the device may be used to release pharmaceutically active materials within the body of a patient after a predetermined time interval. This may be useful in the treatment of medical conditions where it is desirable to administer a pharmaceutically active material to the patient sometime through the night while the patient is asleep, so as to provide a desired level of the drug in the patient in accordance with his needs during the night or when he awakes. It may also be useful to allow administration of materials at a predetermined point as the device passes through the gastro-intestinal tract, for example in the colon.

Patent specification WO92/13521 (Alza Corporation) describes fluid-imbibing dispensing devices for delayed delivery of an active agent, which include an expansion means which absorbs fluid from a surrounding environment. The dispensing device comprises a housing having first and second wall sections telescopically engaged with each other, particularly a capsule having a hollow cap and a hollow body; either the cap or the body is in the form of a male section fitted inside the open end of the other female section. The expansion means is contained within the device and expands as it absorbs fluid, forcing apart the two sections of the device. The expansion means may be a swellable polymer or an osmotic formulation which swells as it absorbs fluid. In order to allow fluid to come into contact with the expansion means contained within the device, one of the wall sections adjacent to the expansion means is fluid-permeable. After the sections are disengaged, fluid enters the device and comes into contact with the active agent contained within the device, thereby dispensing the active agent into the fluid.

In order for the device to function correctly, the active material contained within the female body should be released promptly after the male member has become disengaged. This is dependent on the active material dissolving rapidly in the aqueous medium whilst the active agent is still within the female body, or depends on the material being quickly flushed out of the hollow female body. This in turn requires an active agent which has good solubility in water and/or an adequate supply of aqueous medium. However, there may be instances where the supply of aqueous medium in the patient's body is limited. For example, in the colon insufficient aqueous medium may be present for the device to operate as desired.

U.S. Pat. No. 4,957,494 discloses a dispenser for use in a fluid environment which is intended to release pulses of active agent over a long time period. The construction comprises a housing containing a plurality of layers of active material which are driven towards an outlet of the housing by a fluid actuated driving means. The driving means may include a fluid-swellable polymer, and the portion of the housing next to the driving means has a controlled permeability to fluid i.e. water, such that the rate of swelling of the polymer is controlled by the rate of ingress of water. However, the arrangement is complex and is intended to release the active agent very slowly over an extended period (e.g. at least 21–30 days) rather than to provide a very rapid release of active material.

It is an object of the present invention to mitigate these problems, by providing a system which rapidly positively expels the contents from the body.

SUMMARY OF THE INVENTION

In one aspect, the present invention provides a delivery device for delivering a substance, which comprises a hollow body containing the substance to be delivered, together with an expandible excipient whose volume expands rapidly in contact with an aqueous medium such as to expel the substance from the body.

The function of the expandible excipient is to positively expel the substance rapidly and substantially completely from the body, such as to provide reproducible delivery times.

The hollow body is preferably provided with a cap (for example, a hard gelatin cap), which dissolves soon after the hollow body has been administered to a patient, thereby allowing access of the aqueous medium.

Preferably, the device further comprises a male member engaged within a neck portion of the (female) body, the device including a water-swellable material which swells so as to disengage the female body upon exposure of the device to the aqueous medium, and thereby allows the aqueous medium to come into contact with the expandible excipient within the female body.

In one embodiment, the hollow body is provided with a male plug engaged within a neck portion of the (female) hollow body, the male plug being formed of a water-swellable material which swells so as to disengage the female body upon exposure to the aqueous medium. The time taken for the plug to become disengaged (i.e. the "pulse" time) determines the time at which aqueous medium enters the body and contacts the active substance to be delivered. The plug is preferably formed of a water-swellable hydrogel such as described in WO90/09168.

In another embodiment, the male member is a hollow member closed at one end, whose opposite open end engages within the neck of the female body. A water swellable material is provided within the device which serves to disengage the female member after a predetermined time, by forcing the male member and the female body apart as the material swells in the presence of water. The swellable material inside the device may be an osmagent or an osmopolyer. Such an arrangement is disclosed in WO92/13521. In order to allow water to enter the device and to contact the water-swellable material a portion of the wall of the device adjacent thereto is preferably semipermeable; that is to say it is permeable to the passage of water into the device but impermeable to release of other substances from within the device.

The walls of the hollow female body may be formed from a wide variety of materials. They may be of homogenous constructions or they may be laminated. Examples of materials suitable for use in the construction of the body include polyethylene, polypropylene, poly(methylmethacrylate), polyvinyl chloride, polystyrene, polyurethanes, polytetrafluoroethylene, nylons, polyformaldehydes, polyesters, cellulose acetate and nitro cellulose.

However, a preferred construction uses an impermeable coating to cover the exterior of a body formed from a water soluble material. The coating may conveniently be formed by dipping a body in a solution of a material which forms a layer which is impermeable to water. Alternatively, the body might be spray-coated. A preferred class of bodies are conventional hard gelatin or starch capsule bodies coated with a solution of polyvinyl chloride or a polyvinyl acetate copolymer, or an ethyl cellulose solution.

Preferably, the expandible excipient is a solid material whose volume increases due to the absorption of water from the surrounding aqueous medium. The solid material is preferably particulate to assist uptake of water.

In one preferred form, the expandible excipient is a water-swellable hydrogel material. Preferred hydrogel materials are mentioned in WO90/09168 and include poly (hydroxyethyl-methacrylate), poly(N-vinylpyrrolidone), and polyurethanes. A particularly preferred class of hydrogels are those cross-linked hydrophilic polymers comprising polyethylene oxide residues. Chemical cross-linking may be effected in known manner. Where the hydrophilic polymer comprises functional groups which comprise an active hydrogen atom, chemical cross-linking may be effected by means of di- or polyisocyanates. Preferably, the polyethylene oxide residues have a number average molecular weight greater than 1500, preferably greater than 3,000, and most preferably from 4,000 to 12,000. Particularly preferred polyurethane materials are formed by polymerising a polyethylene glycol with a $C_6$–$C_{10}$ alkanetriol, and a diisocyanate.

It has been found that hydrogel particles formed by grinding tend to have rough and irregular particle shapes. Such ground particulate hydrogel does not have the ideal handling properties expected of a pharmaceutical excipient. In particular, it has poor flow properties. This makes handling and accurate delivery difficult. Delivery of measured amounts of powder is often carried out in industrial filling machines by sucking powder into a measure of known volume, and then emptying out the measured volume of powder. This requires a powder of good flow properties, in order that the known volume always contains the same amount of powder.

The flow properties of the ground hydrogel particles may be improved by coating the hydrogel particles with a coating material which improves the regularity of the particles. The coating material should not unduly restrict access of water to the hydrogel so as not to detract from the swellability of the hydrogel, and is therefore preferably hydrophilic or water-soluble. Preferred coating materials include carbohydrates such as monosacharrides, polysacharrides, sugars, starches and celluloses. Wetting agents may also be included. In fact such coatings have also been found to improve the speed of water-uptake by the hydrogel particles.

The coating may be 0.5–20 wt % of the coated hydrogel particle.

Another aspect of the invention relates to the use of hydrogel particles as an expandible excipient in a solid pharmaceutical dosage form. Optionally, the hydrogel particles are coated as described above. The solid pharmaceutical dosage forms are generally compressed powders (such as tablets) or cast forms (such as pessaries). A further aspect of the invention thus relates to a solid pharmaceutical dosage form comprising the optionally coated hydrogel particles.

Alternatively, the expandible excipient may be chosen from the class of pharmaceutical disintegrants, which are known substances. Disintegrants are known pharmaceutical expedients and are often included in solid dosage form (such as tablets or pessaries) in order to enhance the rate of delivery of an active substance contained therein. The disintegrants are water-swellable substances which absorb water after administration to a patient and swell rapidly, thereby disrupting or breaking-up the solid dosage form.

Suitable disintegrants include starches, celluloses, and polyvinylpyrrolidone. The starches and celluloses may be chemically modified, as known in the art. Chemically modified starches include carboxymethyl starch. Partly pregelatinised starch may also be used. Explotab (trademark) is a sodium starch glycollate. The cellulose may be a microcrystalline cellulose (such as that available under the trademark AVICEL). Chemically modified celluloses include carboxymethyl cellulose (such as that available under the trademark Ac-di-sol) and cellulose 2-hydroxypropyl ethers (such as low-substituted 2-hydroxypropyl ethers available, for example, under the trademarks LHPC11 and LHPC21). Suitable polyvinylpyrrolidones are available under the trademark Kollidone CL.

The expandible excipient may include minor amounts of formulation adjuncts. Wetting agents (e.g. sodium lauryl sulphate) may be included, usually in amounts up to 2% by weight. Flow agents such as magnesium stearate and fumed silica may be included, generally in amounts up to 1% by weight. Water-soluble materials such as sugars or other carbohydrates may be included, generally in amounts of up to 10% by weight. Wicking agents such as those materials already mentioned as disintegrants (e.g. microcrystalline cellulose) may be included if necessary to enhance the speed of water uptake, preferably in amounts up to 10% by weight.

Preferably, the expandible excipient has an overall swelling capacity of greater than 200%, preferably greater than 300% and advantageously more than 400%. This percentage swellability represents the final percentage increase in volume over and above the original volume at equilibrium.

The expandible excipient will preferably remain in a solid or gelled phase until the substance to be delivered has been expelled. Thereafter, it may in some circumstances be acceptable for the excipient to dissolve partially or completely in the aqueous environment.

The excipient may be present as a particulate material, e.g. of particle size 50 to 500 microns. Generally the particles will have been produced by grinding and have a broad particle size distribution. However, the size distribution may be narrowed by sieving. The particles may either agglomerate when water is absorbed or may be non-agglomerating. Agglomeration may improve the gel strength and prevent the substance which is to be expelled from becoming trapped in the gel. However, non-agglomeration may be preferred in the case of expandible hydrogel excipients in order to maintain a network of channels through which aqueous medium can flow into the hydrogel mass.

The excipient may also be granulated to improve its handling properties.

For ease of filling into the hollow body, the expandible excipient is preferably formed into a solid form, for example by compressing into a slug or tablet. The hardness of the compressed solid slug form may be less than for conventional tablets (e.g. a hardness of 0–2 kg as opposed to at least 4 kg for conventional tablets). The solid compressed form may be formed by compression of powder in a conventional filling machine.

The object of the expandible excipient is to expel the substance from the body rapidly and completely. It is therefore necessary to employ an excipient whose rate of expansion and degree of expansion in contact with aqueous medium are adequate. In particular it is preferred that the rate of expansion over the first minute (generally the rate decreases thereafter) is greater than 50%, preferably greater than 100% and especially greater than 150% per minute. Preferably the degree of expansion in the first three minutes is greater than 75%, preferably greater than 130% and especially greater than 200%. Methods for determining these parameters are given herein.

The expandible excipient will preferably have a speed of wicking in a solid compact of at least 1.0, preferably at least 2.0, ml of water uptake per 500 mg of excipient according to the method described by Nogami et al. (Chem. Pharm. Bull., 17(7), 1450–1455, (1969)).

Generally, the invention will find the greatest application in the expulsion of solid substances, though use with liquids cannot be excluded. The solid substance may be in any of the formulation forms known in the art, such as tablet, powder, granules or pellets; or may be a capsule (e.g. a hard gelatin or soft gelatin capsule) containing a liquid to be delivered.

In a particularly preferred embodiment, the substance to be delivered is present (e.g. in a discrete layer or as pellets or a tablet) which lies above the expandible excipient. In this way, as the excipient expands, the substance is expelled first by the expanding excipient. In other words, the substance is located closest to the mouth of the hollow body. Naturally, if more than one substance to be delivered is present, the various substances may be arranged in different layers.

The invention also relates to a method of expelling a substance to be delivered from a hollow body, which comprises providing said substance within the hollow body together with an excipient whose volume expands rapidly when in contact with an aqueous environment such as to expel the substance.

The presence of the expandible excipient has been found to result in improved expulsion of the active substance from a capsule, and more reproducible delivery time, particularly in regions of the gastro-intestinal tract which have a relatively low water content.

Preferably the time for expulsion of the contents of the capsule is short (e.g. 0.5 to 20 mins, preferably 1 to 5 mins) compared to the pulse time, and is usually shorter than the dissolution time of the substance such that the substance is expelled first and then becomes dissolved in aqueous medium.

BRIEF DESCRIPTION OF THE DRAWINGS

Embodiments of the invention will now be described by way of example only.

FIG. 1a, 1b and 1c are cross-sections of various tablet shapes for use in the delivery device;

DETAILED DESCRIPTION OF THE PREFERRED EMBODIMENTS

Figure 1:
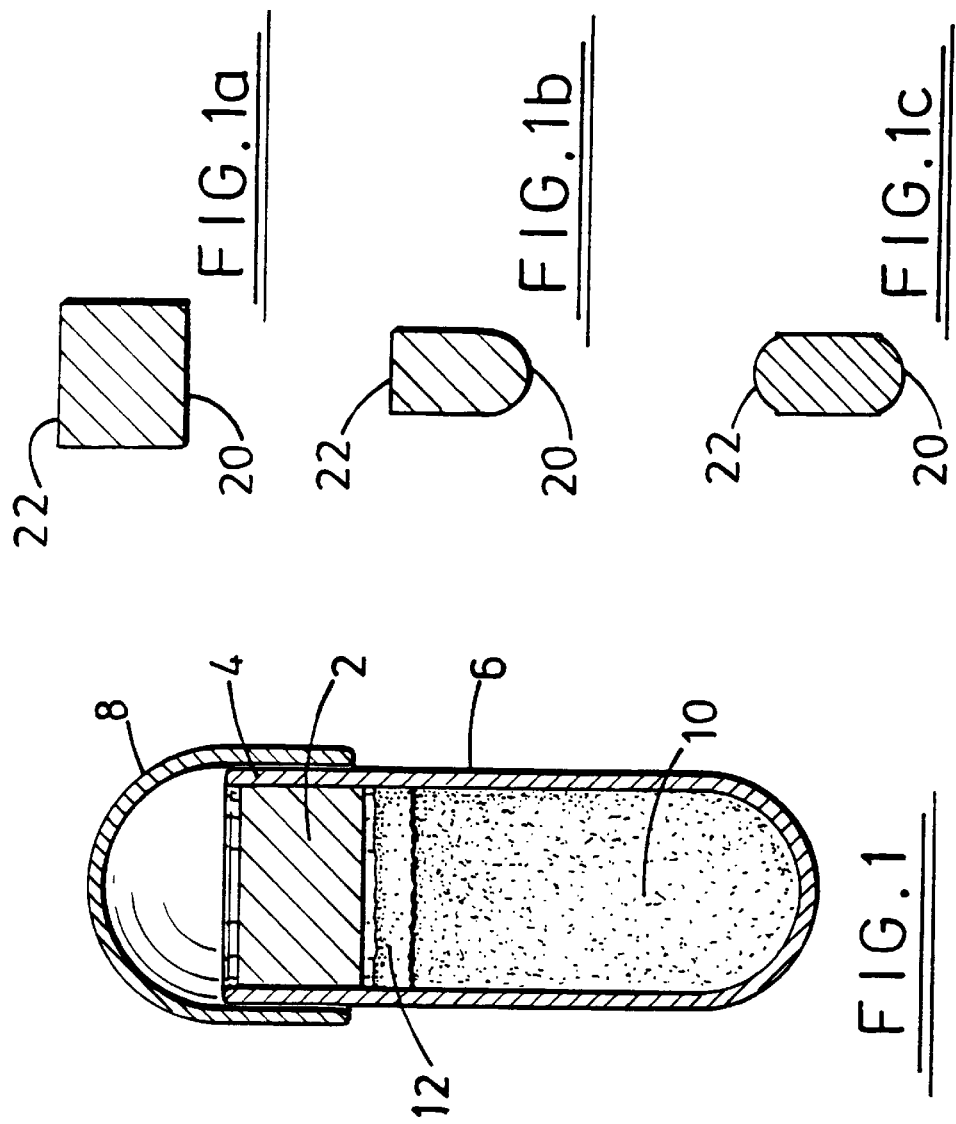
FIG. 1 is a cross section to an enlarged scale of a delivery device according to the present invention in the form of a capsule.

The capsule shown in FIG. 1 comprises a male plug 2 formed of a hydrogel material of the type disclosed in Example 1, inserted in neck 4 of hollow female body 6. The capsule is closed with a cap 8 of water-soluble material, such as a hard gelatin cap.

The male plug 2 is inserted so that the upper end of the plug is proud of, level with or recessed below the upper end of the neck 4. The cap 8 is formed of a water-soluble material which dissolves quickly in the stomach after administration to the patient. The body 6 is formed of a water-insoluble material, which may be a water-insoluble plastics material or may be gelatin coated with a water-impermeable coating (such as disclosed in WO90/09168).

A lower layer 10 of expandible excipient in the form of non-agglomerating hydrogel particles according to Example 1 is packed into the body 6. A layer 12 of pharmaceutically active substance to be delivered (with or without an inert pharmaceutically acceptable carrier material) is positioned on top of the hydrogel layer.

When the capsule is administered to a patient, the aqueous environment in the gastro-intestinal tract quickly dissolves the water soluble cap. Water is then absorbed into the hydrogel plug 2, which swells and is expelled from the body after a predetermined time interval (for example 2 to 10 hours). This allows the contents of the capsule to be released into the patient's gastro-intestinal tract.

Release of the contents is assisted by swelling of the hydrogel 10 as aqueous fluid enters the body 6. Thus, the layer of hydrogel quickly absorbs aqueous fluid and expands, expelling the layer 12 of pharmaceutically active substance from the body and delivering it into the gastro-intestinal tract.

FIGS. 1a, 1b and 1c show suitable tablet shapes (in cross-section) for use in the capsule shown in FIG. 1 in place of the hydrogel particles. The tablets are typically formulated as in Example 10.

FIG. 1a shows a tablet having a flat bottom surface 20 and flat upper surface 22.

FIG. 1b shows a tablet having a flat upper surface 22 and a curved bottom surface 20 which corresponds to the curvature of the bottom of the capsule body 6 so as to fit neatly therein.

FIG. 1c shows a similar tablet where both the bottom and top surfaces are curved so as to fit neatly into the bottom of the capsule but without requiring orientation thereof by the capsule filling machine.

EXAMPLE 1

Hydrogel rods were prepared by batch polymerising 6,000 grams of polyethylene glycol PEG 8000 (Pharma) of number molecular weight Mn 8700 and ratio Mw/Mn=1.03 (where Mw is the mean molecular weight) with 111.04 grams of hexanetriol, 506.8 grams of Desmodur W (dicyclohexylmethane-4,4-diisocyanate), and catalysed by 0.6 grams of anhydrous ferric chloride. The mole ratios were PEG 8000 (1 mole), hexanetriol (1.2 moles), Desmodur W (2.8 moles) and ferric chloride (0.01% by weight of PEG). The PEG 8000 was melted and dried to less than 0.05% w/w moisture content in a Buchi Rotavapor at 95° C., at a pressure less than 5 millibars for a period of two hours. Then, the ferric chloride was dissolved in the hexanetriol at 75° C., and the mixture stirred into the dried PEG for 5 minutes at 100 rpm. The mixture at 85° C. was then mixed with the Desmodur W in a mixer at 1500 rpm for 30 minutes. Molten polymer at about 80° C. was then dispensed into tubular polytetrafluoroethylene moulds 25 cm long and internal diameter about 6.7 mm under a vacuum of less than 50 millibars. Curing took place at 95° C. for 4 hours in a fan equipped oven. The hydrogel polymer rods were then allowed to cool.

The hydrogel rods are washed by immersion in a circulating stream of water containing butylated hydroxy amisole (BHA) as a stabiliser. The washing removed water-soluble extractable substances from the polymer and the BHA stabiliser becomes incorporated into the polymer.

The swelling factor is defined as $(W_s-W_d)/W_d \times 100$, where $W_s$ is the swollen volume and $W_d$ is the dry volume. The hydrogels were found to have a swelling factor of 270±25.

The hydrogel was ground and then sieved to produce a powder having a particle size in the range 425 to 710 microns.

EXAMPLE 2

(Drug Release-hydrogel Excipient)

A coated gelatin capsule of the type shown in FIG. 1 was filled with hydrogel powder prepared as in Example 1 of particle size 425 to 710 microns, and metoclopramide drug included as a separate layer. The hydrogel powder was compacted leaving a 4.5 mm space between the top of the hydrogel layer 10 and the mouth of the body 6. The metoclopramide was placed on top and the body was sealed with a hydrogel plug. The hydrogel plug had a nominal length 4.0 mm and a nominal diameter of 6.8 mm, and the top of the plug was flush with the mouth of the body 6. The nominal delivery time was three hours.

In order to assess the delivery time to release of the drug, each capsule was placed in a liter of purified water at 37° C. stirred with a paddle at 50 rpm. The presence of drug in the water was monitored spectrophotometrically. The results for six capsules are given in Table 1. These show a mean delivery time of 3.21 hours with a standard deviation of 0.10. This low standard deviation represents reproducible delivery times.

TABLE 1

| | Weight of Fill (mg) | Weight of metoclopramide (mg) | Plug Length (mm) | Plug Dia (mm) | Delivery Time (hrs) |
|---|---|---|---|---|---|
| 1. | 250.2 | 4.4 | 3.99 | 6.77–78 | 3.25 |
| 2. | 249.9 | 4.0 | 4.00 | 6.76–81 | 3.00 |
| 3. | 250.4 | 4.6 | 3.97 | 6.74–81 | 3.25 |
| 4. | 250.7 | 4.4 | 4.01 | 6.76–79 | 3.25 |
| 5. | 250.7 | 4.5 | 3.97 | 6.75–77 | 3.25 |
| 6. | 250.0 | 4.3 | 4.02 | 6.76–78 | 3.25 |

(Mean = 3.21)
(Standard deviation = 0.10)

EXAMPLE 3

(Hydrogel Excipient)

The procedure was repeated with a capsule having a hydrogel plug designed to provide a nominal delivery time of five hours. The active material was salbutamol sulphate. The mean delivery time was 5.57 hrs., with a standard deviation of 0.36. The details are given in Table 2. The "space" represents the space between the top of the hydrogel layer and the mouth of the body after inclusion of the drug. The space allows insertion of the plug to its correct depth without interference from the hydrogel powder fill. In this case the hydrogel plug was recessed 0.5 mm below the upper end of the neck of the capsule body.

TABLE 2

| | Wt Capsule (mg) | Wt Hydrogel (mg) | Wt Drug (mg) | Space (mm) | Plug Length (mm) | Plug dia (mm) | Plug Recess (mm) |
|---|---|---|---|---|---|---|---|
| 1. | 109.9 | 145.0 | 9.7 | 5.5 | 3.99 | 6.87–6.90 | 0.5 |
| 2. | 109.9 | 144.8 | 10.3 | " | 3.95 | 6.88–6.90 | " |
| 3. | 109.9 | 145.0 | 10.1 | " | 3.95 | 6.87–6.90 | " |
| 4. | 109.2 | 145.3 | 10.2 | " | 3.95 | 6.87–6.91 | " |
| 5. | 109.2 | 144.9 | 10.0 | " | 4.02 | 6.88–6.92 | " |

Drug release was monitored spectrophotometrically at 226 nm.

EXAMPLE 4

(Hydrogel Excipient)

The procedure of Example 2 was repeated also with salbutamol sulphate, but with a shorter plug to give a nominal three hour pulse time. The mean pulse time was 3.29 hrs. with a standard deviation of 0.1. The details are given in Table 3.

TABLE 3

| | Wt Capsule (mg) | Wt Hydrogel (mg) | Wt Drug (mg) | Space (mm) | Plug Length (mm) | Plug dia (mm) | Plug Recess (mm) |
|---|---|---|---|---|---|---|---|
| 1. | 104.2 | 145.2 | 10.1 | 5.5 | 3.04 | 6.87–6.91 | 0.5 |
| 2. | 104.9 | 145.5 | 9.8 | " | 3.00 | 6.88–6.91 | " |
| 3. | 104.4 | 144.8 | 9.9 | " | 2.97 | 6.87–6.91 | " |
| 4. | 103.8 | 145.0 | 10.2 | " | 3.01 | 6.86–6.91 | " |
| 5. | 104.2 | 145.2 | 10.1 | " | 3.05 | 6.88–6.92 | " |
| 6. | 103.8 | 145.4 | 9.9 | " | 3.01 | 6.87–6.91 | " |

EXAMPLE 5

(Disintegrant Excipient)

Figure 2:
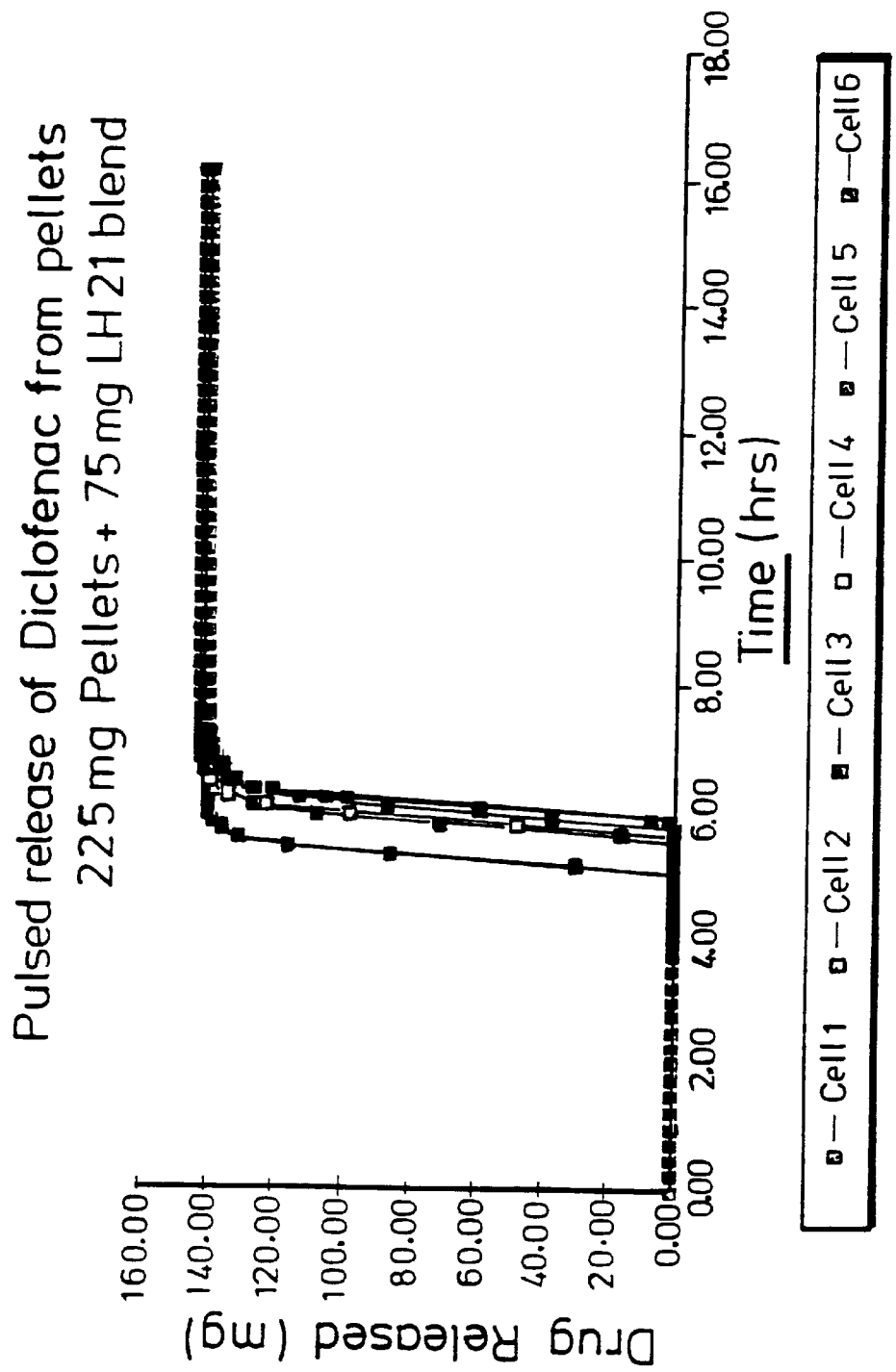
FIG. 2 shows a drug release profile from Example 5.

The procedure of Example 2 was repeated using a capsule fill comprising 75 mg of an LHPC21 expandable excipient disintegrant blend as in Example 7, with a layer of 225 mg pellets of diclofenac (containing 140 mg of diclofenac sodium) on the expandable excipient. The release profile of the diclofenac monitored spectrophotometrically for six samples (cells) is shown in FIG. 2. Diclofenac sodium is 2-[(2,6-dichlorophenyl)amino] benzene acetic acid monosodium salt.

EXAMPLE 6

(Hydrogel Powder Formulation)

A suitable expandable excipient was made by admixing the following weight percentages:
  hydrogel powder-balance
  sodium lauryl sulphate
    (wetting agent)-1% magnesium stearate
 (flow agent)-0.5% avicel (wicking agent)-5%

The hydrogel powder had been coated in an Aerocoater (trademark) fluidised bed spray coating machine with 5 wt % lactose. The lactose was dissolved in a minimum amount of water and then made up to 5 wt % solution with a 50:50 mixture of isopropyl alcohol and acetone. The hydrogel powder was spray coated with the solution and then dried.

EXAMPLE 7

(Disintegrant Slug Formulation)

An expandible excipient was made up as follows. The following were admixed in the weight percentages given:

LHPC21 (disintegrant)-balance sodium lauryl sulphate
 (wetting agent)-1% magnesium stearate
 (lubricant)-0.5%

LHPC21 is a low-substituted 2-hydroxypropyl ether cellulose, and is available from Shin-Etsu, Tokyo, Japan.

The mixture was then compressed into a slug on a Zanasi capsule assembly machine.

EXAMPLE 8

(Disintegrant Slug Formulation)

A further expandible excipient was made up as follows for use in subsequent scintigraphic and pharmacokinetic studies. The following mixture was made up in the weight percentages given:

low-substituted hydroxypropyl
 cellulose (LHPC21) 98.5%

Sodium lauryl sulphate 1.5% magnesium stearate 0.5%

The formulation was made into slugs using a hand-operated machine.

EXAMPLE 9

(Disintegrant Slug Formulation)

A further expandible excipient particularly suitable for compression into slugs on a capsule filling machine was prepared as follows, percentages being by weight:

LHPC21 88.0%

Avicel 200 10.0%

Sodium lauryl sulphate 2.0%

This was formed into slugs on a Zanasi capsule filling machine.

AVICEL (trademark) is a microcrystalline cellulose material available from FMC Corporation, USA.

EXAMPLE 10

(Disintegrant Tablet Formulation)

An expandible excipient in the form of a tablet was typically prepared from the following (percentages by weight):

|  | (i) | (ii) |
|---|---|---|
| LHPC21 | 49.0 | 24.0 |
| Avicel 200 | 49.0 | 24.0 |
| Explotab | — | 50.0 |
| Sodium lauryl sulphate | 2.0 | 1.0 |
| Sodium stearyl fumarate | — | 1.0 |

EXPLOTAB (trademark) is sodium-starch-glycollate and is available from Forum Chemicals, Reigate, U.K.

Formulation into a tablet (rather than ex-tempore slug production on the capsule filling machine itself) enables the excipient tablets to be pre-prepared and fed to the capsule filling machine as a separate component.

Suitable tablet shapes are shown in FIGS. 1a, 1b and 1c. The diameter is generally in the range 6.0 to 6.65 mm and the length is 3 to 12 mm.

EXAMPLE 11

(Disintegrant Slug Comparison Tests)

The emptying of a capsule body of the type shown in FIG. 1 was compared with and without a disintegrant expandible excipient.

In the comparison test, pellets containing 75 wt % diclofenac sodium were filled into a capsule body.

According to the invention, a slug containing 100 mg LHPC disintegrant according to Example 8 was placed in the capsule body and 150 mg of the diclofenac sodium pellets were filled above the disintegrant slug.

The two types of capsules were then closed with a hydrogel plug and placed in a vessel containing 1 l of water at 37° C. stirred by a paddle at 50 rpm. The plugs disengaged and the % diclofenac sodium released after quarter hour intervals was measured spectrophotometrically. The results in Table 4 show that in the capsule of the invention emptying was essentially complete after 0.25 hr whereas in the comparison the capsule was still only half empty one hour after disengagement of the plug.

TABLE 4

|  | % released after (hrs) | | | |
|---|---|---|---|---|
|  | 0.25 | 0.5 | 0.75 | 1.0 |
| 230 mg pellets (comparison) | 34.44 | 40.15 | 47.83 | 54.53 |
| 150 mg pellets/100 mg disintegrant | 99.81 | 99.97 | 100.00 | — |

EXAMPLE 12

(In Vivo Scintigraphy)

This study investigated the expulsion of the contents of a delivery device of the type shown in FIG. 1 in vivo in human volunteers. The contents were radiolabelled to allow their progress to be monitored.

The delivery devices shown in Table 5 were used:

TABLE 5

| | Expandible Excipient | Substance delivered (label) |
|---|---|---|
| 1) | hydrogel powder (Ex 6) | 75 mg tablet ($^{111}$In) |
| 2) | hydrogel powder (Ex 6) | 75 mg pellets ($^{99}$Tc) |
| 3) | disintegrant slug (Ex 8) | 75 mg tablet ($^{111}$In) |
| 4) | disintegrant slug (Ex 8) | 75 mg pellets ($^{99}$Tc) |

Nominal delivery time=2 hrs
(A further four devices had a nominal delivery time=4 hrs)

Seven healthy volunteers were each dosed on each of four occasions with a delivery device of nominal delivery time 2 hrs and one of nominal delivery time 4 hrs. On the four occasions a device of type 1 to 4 respectively as set out in Table 5 was administered. Scintigraphic images of each volunteer were taken every half hour using a gamma radiation camera throughout the study day to enable transit of the device through the gastro-intestinal tract and release of the radiolabel to be monitored.

At 2 and 4 hours respectively following administration, the devices were found to be located in various regions of the gastro-intestinal tract i.e. stomach, small intestine and colon. Prior to disengagement of the plug, the scintigraphic image was small and bright. Release and subsequent dispersion of the labelled pellets or tablet from the capsule body was clearly seen by the spread of the radiolabel. The average release time was 123 mins (standard deviation 26) for the device of nominal release time 2 hrs, and 275 mins (standard deviation 28) for the 4 hr device.

EXAMPLE 13

(In-vivo Pharmacokinetic Study)

The objective was to investigate the absorption profile in plasma of salbutamol contained in a delivery device of the type shown in FIG. 1, of nominal release time 4 hrs in human volunteers.

Eleven healthy volunteers were dosed by mouth on separate occasions with a device of nominal release time 4 hrs, and for comparison purposes with a conventional immediate release tablet. The delivery device contained a disintegrant slug (Example 8) and a 4 mg salbutamol tablet above the slug. The immediate release tablet also contained 4 mg salbutamol.

Figure 3:
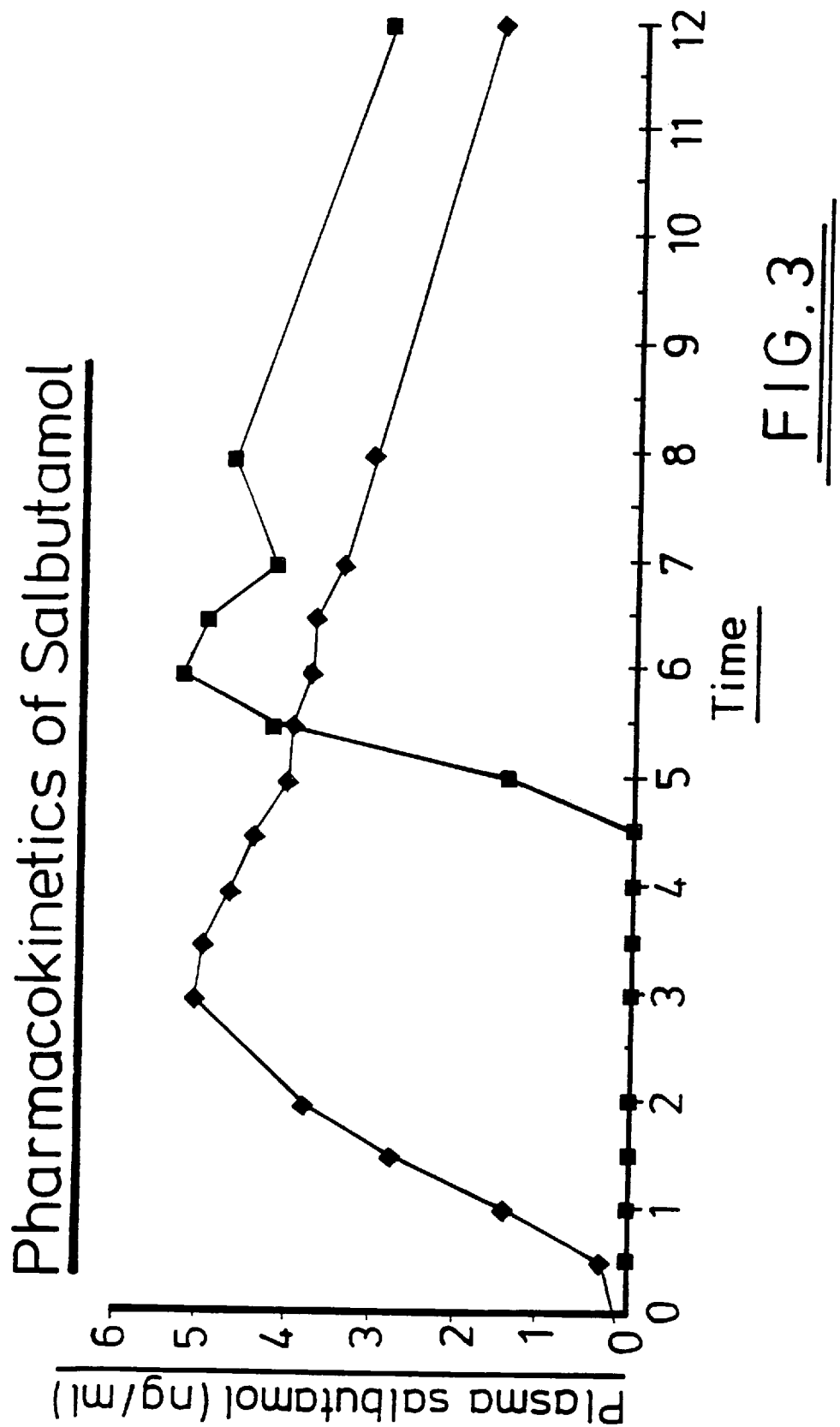
FIG. 3 is the results of a pharmacokinetic study on salbutamol release in-vivo from a delivery device of the invention.

In each volunteer salbutamol was detected in the plasma following release of the salbutamol from the immediate release tablet and from the delivery device. The pharmacokinetic data are shown in FIG. 3, where the circles indicate the immediate release tablet and the squares indicate the 4 hr delivery device. In both cases the release profile is similar and correspond to expected literature values. Thus, the delivery device has quickly released the salbutamol following plug disengagement, and without substantially affecting the release profile. Had the release not been quick, a less steep release curve would have resulted.

EXAMPLE 14

(Evaluation of Expandible Excipients)

In order to be suitable, an expandible excipient (e.g. a hydrogel powder or a disintegrant) should be capable of rapidly expelling the active substance from the capsule body once the plug has disengaged. This requires that the excipient should expand rapidly on contact with water and also requires a sufficiently high degree of expansion. Certain materials were tested as suitable excipients using the following methodologies.

(i) Degree and Rate of Expansion

A Lloyds LRX materials tester with a 50N load cell was used to assess the rate and degree of expansion of potential excipients. A 1 g sample of the excipient was placed in a well in a metal block. A perforated plate attached to the load cell was lowered down onto the sample, applying a pre-load of 1N to compress the sample. Water was then added to the sample via the perforated plate and was absorbed by the sample. Any expansion of the sample caused a movement of the plate.

Measurements were taken on a group of five samples of each excipient as follows:
depth of sample (mm)
rate (mm/min) over first minute
total expansion (mm) at 3 mins The results are given in Table 6.

From the Table, it can be seen that two excipients (CaCMC and Protacid-F120) have a low degree of expansion and a slow rate of expansion and are not favoured for use in the present invention. CaCMC stands for calcium carboxymethyl cellulose. Protacid is alginic acid and is available from Pronova Biopolymer A. S., Drammen, Norway.

(ii) Time for expulsion from capsule

A 200 mg sample of the excipient was placed into a capsule body and lightly packed down. A small ball of Blue Tac (trademark) rubber adhesive material (approximately 75 mg and 5 mm in diameter) was then placed in the capsule on top of the excipient. The capsule body was held vertically in a metal block within a beaker and water was slowly added until the capsule was submerged in the water. Any air bubbles formed were dislodged with a jet of water. The time taken for the ball of Blue Tac to be expelled from the capsule body after the water had contacted the expandible excipient was recorded. The results are shown in Table 6. Again, CaCMC and Protacid have long expulsion times and are not favoured.

TABLE 6

(expandible excipients)

| Material | % Expansion (3 mins) | Initial Rate (1st min) of Expansion (%/min) | Time for Expulsion (secs) |
|---|---|---|---|
| LHPC.11 | 160 | 160 | 33 |
| LHPC.21 | 250 | 250 | 17 |
| LHPC.31 | 250 | 250 | 40 |
| HYDROGEL POWDER | 140 | 70 | 150 |
| AC.DI.SOL | 150 | 90 | 500 |
| CaCMC | 63 | 30 | >600 |
| PROTACID.F120 | 85 | 70 | >600 |
| EXPLOTAB | 250 | 230 | 55 |

We claim:
1. A delivery device for delivering a substance which comprises a water impermeable hollow female body (6) having a neck portion and containing the substance (12) to be delivered, together with an expandable material (10) whose volume expands rapidly in contact with an aqueous medium in order to positively expel the substance from the female body, the expandable material being present in a lower layer within the female body and the substance to be delivered being present in a upper layer closer to the neck portion of the female body; and a water-swellable male member (2) engaged with the neck portion (4) of the hollow female body which swells so as to disengage the hollow female body upon exposure of the device to the aqueous medium and thereby allows the aqueous medium to come into contact with the expandable material (10) within the hollow female body.

2. A device according to claim 1 wherein the expandible material is a solid material whose volume increases due to absorption of water from the aqueous environment.

3. A device according to claim 2 wherein the solid expandible material is in particulate form.

4. A device according to claim 3 wherein the solid expandable material has a particle size in range the range 50 to 500 microns.

5. A device according to claim 1 wherein the expandable material is a hydrogel.

6. A device according to claim 5 wherein on absorption of water the hydrogel particles swell into a porous network having channels therein which continue to allow access of said aqueous medium thereto.

7. A device according to claim 5 wherein the hydrogel is a polyurethane prepared from a polyethylene glycol, a $C_6$–$C_{10}$ alkanetriol and a diisocyanate.

8. A device according to claim 7 wherein the polyurethane is prepared from a polyethylene glycol having a number average molecular weight of 4000 to 12,000, hexanetriol and dicyclohexylmethane-4,4-diisocyanate.

9. A device according to claim 6 wherein the hydrogel is comprised of coated particles.

10. A device according to claim 9 wherein the particles are covered with a coating material selected from the group consisting of: monosaccharides, polysaccharides, sugars, starches and celluloses.

11. A device according to claim 10 wherein the coating materials comprises 0.5 to 20 wt % of the coated particle.

12. A device according to claim 1 wherein the expandable material is a pharmaceutical disintegrant.

13. A device according to claim 12 wherein the disintegrant is selected from the group consisting of starches, celluloses and polyvinylpyrrolidone.

14. A device according to claim 13 wherein the disintegrant is a low-substituted 2-hydroxypropyl ether cellulose.

15. A device according to claim 1 wherein the substance is substantially completely expelled from the body in 0.5 to 5 mins.

16. A device according to claim 1 wherein the male member is a plug, and the plug is formed of a water swellable material.

17. A device according to claim 16 wherein the plug is formed of a hydrogel.

* * * * *